(12) United States Patent
Yang et al.

(10) Patent No.: US 12,150,946 B2
(45) Date of Patent: Nov. 26, 2024

(54) OPHTHALMIC PHARMACEUTICAL COMPOSITION, OPHTHALMIC KIT, AND PHARMACEUTICAL APPLICATION THEREOF

(71) Applicant: Shenyang Xingqi Pharmaceutical Co., Ltd., Liaoning (CN)

(72) Inventors: Qiang Yang, Liaoning (CN); Jidong Liu, Liaoning (CN)

(73) Assignee: Shenyang Xingqi Pharmaceutical Co., Ltd., Liaoning (CN)

(*) Notice: Subject to any disclaimer, the term of this patent is extended or adjusted under 35 U.S.C. 154(b) by 0 days.

(21) Appl. No.: 16/649,268

(22) PCT Filed: Sep. 20, 2018

(86) PCT No.: PCT/CN2018/106677
§ 371 (c)(1),
(2) Date: Mar. 20, 2020

(87) PCT Pub. No.: WO2019/057110
PCT Pub. Date: Mar. 28, 2019

(65) Prior Publication Data
US 2020/0215079 A1    Jul. 9, 2020

(30) Foreign Application Priority Data
Sep. 22, 2017 (CN) .......................... 201710863869.2

(51) Int. Cl.
*A61K 31/573* (2006.01)
*A61K 9/00* (2006.01)
(Continued)

(52) U.S. Cl.
CPC .......... *A61K 31/573* (2013.01); *A61K 9/0019* (2013.01); *A61K 9/0051* (2013.01);
(Continued)

(58) Field of Classification Search
CPC ...... A61K 31/573; A61K 47/34; A61K 47/10; A61K 9/0051
See application file for complete search history.

(56) References Cited

U.S. PATENT DOCUMENTS 7,618,651 B2    11/2009    Murthy
2006/0009498 A1    1/2006    Whitcup
(Continued)

FOREIGN PATENT DOCUMENTS

CN    1240346 A    1/2000
CN    101031283 A    9/2007
(Continued)

OTHER PUBLICATIONS https://www.mayoclinic.org/drugs-supplements/triamcinolone-intraocular-route/precautions/drg-20524772?p=1; accessed Mar. 8, 2024 (Year: 2024).*
(Continued)

*Primary Examiner* — Timothy P Thomas
(74) *Attorney, Agent, or Firm* — The Webb Law Firm

(57) ABSTRACT

The invention belongs to the field of drug preparations and discloses an ophthalmic sustained-release drug delivery system. The ophthalmic sustained-release drug delivery system consists of biocompatible solid and liquid substances, as well as substances with pharmacological activity and pharmacologically acceptable salt of the substances, and can be mixed with a matrix which is liquid at room temperature, has the density larger than that of water and almost incompatible with water, so that the drug release rate and the degradation time of the delivery system are changed. According to the sustained-release drug delivery system, a drug is solidified into a ball at an eye, so that the drug liquidity is reduced, drug release is sustained, the administration times is reduced, and the compliance of patients is improved.

10 Claims, 5 Drawing Sheets

(51) Int. Cl.
| | |
|---|---|
| A61K 31/216 | (2006.01) |
| A61K 31/506 | (2006.01) |
| A61K 47/10 | (2017.01) |
| A61K 47/34 | (2017.01) |
| A61K 47/60 | (2017.01) |
| A61K 9/10 | (2006.01) |
| A61K 45/06 | (2006.01) |

(52) U.S. Cl.
CPC .......... *A61K 31/216* (2013.01); *A61K 31/506* (2013.01); *A61K 47/10* (2013.01); *A61K 47/34* (2013.01); *A61K 47/60* (2017.08); *A61K 9/10* (2013.01); *A61K 45/06* (2013.01)

(56) References Cited

U.S. PATENT DOCUMENTS

| | | | |
|---|---|---|---|
| 2012/0022137 | A1 | 1/2012 | Rivers et al. |
| 2018/0092836 | A1* | 4/2018 | Utkhede ............... A61F 9/0017 |

FOREIGN PATENT DOCUMENTS

| | | | |
|---|---|---|---|
| CN | 101234084 | A | 8/2008 |
| CN | 102178644 | A | 9/2011 |
| CN | 103860466 | A | 6/2014 |
| CN | 104398473 | A | 3/2015 |
| CN | 104958762 | A | 10/2015 |
| CN | 107595765 | A | 1/2018 |
| JP | 2008501757 | A | 1/2008 |
| JP | 2011530568 | A | 12/2011 |
| JP | 2013506683 | A | 2/2013 |
| KR | 20020003738 | A | 1/2002 |
| WO | 9832421 | A1 | 7/1998 |
| WO | 2006093758 | A1 | 9/2006 |
| WO | 2015133580 | A1 | 9/2015 |

OTHER PUBLICATIONS

Hemmati et al.; "Update on Steroid-Induced Glaucoma: A review of the literature and tips on managing patients"; Jul./Aug. 2008; Glaucoma Today; 24-26 (Year: 2008).*

Danhier et al., PLGA-based nanoparticles: An overview of biomedical applications, Journal of Controlled Release, 2012, pp. 505-522, vol. 161, doi: 10.1016/j.jconrel.2012.01.043.

International Search Report from corresponding international publication WO2019057110 (PCT/CN2018/106677), dated Nov. 6, 2018.

Ahmadieh et al., "Triamcinolone Acetonide in Silicone-Filled Eyes as Adjunctive Treatment for Proliferative Vitreoretinopathy", Ophthalmology, 2008, pp. 1938-1943, vol. 115, No. 11.

Alkawas et al., "Intraoperative Intravitreal Injection of Triamcinolone Acetonide for Cataract Extraction in Patients with Uveitis", Ocular Immunology & Inflammation, 2010, pp. 402-407, vol. 18, No. 5.

Aydin et al., "Efficacy of intravitreal triamcinolone after or concomitant with laser photocoagulation in nonproliferative diabetic retinopathy with macular edema", European Journal of Ophthalmology, 2009, pp. 630-637, vol. 9, No. 4.

Banerjee et al., "A pilot study of intraocular use of intensive anti-inflammatory; triamcinolone acetonide to prevent proliferative vitreoretinopathy in eyes undergoing vitreoretinal surgery for open globe trauma; the adjuncts in ocular trauma (AOT) trial: study protocol for a randomised controlled trial", Trials, 2013, pp. 1-8, vol. 14, No. 42.

Cheema et al., "Triamcinolone Acetonide as an Adjuvant in the Surgical Treatment of Retinal Detachment With Proliferative Vitreoretinopathy", Ophthalmic Surgery, Lasers & Imaging, 2007, pp. 365-370, vol. 38, No. 5.

Conway et al., "Intravitreal triamcinolone acetonide for refractory chronic pseudophakic cystoid macular edema" J Cataract Refract Surg, 2003, pp. 27-33, vol. 29.

Furino et al., "Triamcinolone-Assisted Pars Plana Vitrectomy for Proliferative Vitreoretinopathy", Retina, The Journal of Retinal and Vitreous Diseases, 2003, pp. 771-776, vol. 23, No. 6.

Gutfleisch et al., "Pars plana vitrectomy with intravitreal triamcinolone: effect on uveitic cystoid macular oedema and treatment limitations", Br J Ophthalmol, 2007, pp. 345-348, vol. 91.

Hikichi et al., "Improvement of Visual Acuity One-year After Vitreous Surgery in Eyes with Residual Triamcinolone Acetonide at the Macular Hole", American Journal of Ophthalmology, 2008, pp. 267-272, vol. 145, No. 2.

Jonas et al., "Intravitreal triamcinolone acetonide as an additional tool in pars plana vitrectomy for proliferative diabetic retinopathy", European Journal of Ophthalmology, 2003, pp. 468-473, vol. 13, No. 5.

Jonas, J. B., "Intravitreal triamcinoloneacetonide for treatment of intraocular oedematous and neovascular diseases", Acta Ophthalmologica Scandinavica, 2005, pp. 645-663, vol. 83.

Jonas et al., "Intravitreal triamcinolone acetonide for treatment of intraocular proliferative, exudative, and neovascular diseases", Progress in Retinal and Eye Research, 2005, pp. 587-611, vol. 24.

Jonas, J. B., "Intravitreal Triamcinolone Acetonide for Diabetic Retinopathy", Dev Ophthalmol., 2007, pp. 96-110, vol. 39.

Özkiris, A., "Intravitreal Triamcinolone Acetonide Injection for the Treatment of Posterior Uveitis", Ocular Immunology and Inflammation, 2006, pp. 233-238, vol. 14.

Özkiris et al., "Intravitreal triamcinolone acetonide for treatment of persistent macular oedema in branch retinal vein occlusion", Eye, 2006, pp. 13-17, vol. 20.

Park et al., "Additional Retrobulbar Triamcinolone Acetonide Injection for Retrobulbar Optic Neuritis Patients", J Korean Ophthalmol Soc, 2013, pp. 117-122, vol. 54, No. 1. (English-Language Abstract).

Parke III et al., "Intraoperative intravitreal triamcinolone decreases macular edema after vitrectomy with phacoemulsification", Clinical Ophthalmology, 2012, pp. 1347-1353, vol. 6.

Sevim et al., "Intravitreal Triamcinolone Acetonide Versus Pars Plana Vitrectomy for Pseudophakic Cystoid Macular Edema", Current Eye Research, 2012, pp. 1165-1170, vol. 37, No. 12.

Sonoda et al., "Pars plana vitrectomy assisted by triamcinolone acetonide for refractory uveitis: a case series study", Br J Ophthalmol, 2003, pp. 1010-1014, vol. 87.

Ueno et al., "Long-term clinical outcomes and therapeutic benefits of triamcinolone-assisted pars plana vitrectomy for proliferative vitreoretinopathy: A case study", European Journal of Ophthalmology, 2007, pp. 392-398, vol. 17, No. 3.

* cited by examiner

OPHTHALMIC PHARMACEUTICAL COMPOSITION, OPHTHALMIC KIT, AND PHARMACEUTICAL APPLICATION THEREOF

CROSS-REFERENCE TO RELATED APPLICATIONS

This application is the United States national phase of International Application No. PCT/CN2018/106677 filed Sep. 20, 2018, and claims priority to Chinese Patent Application No. 201710863869.2 filed Sep. 22, 2017, the disclosures of which are hereby incorporated by reference in their entirety.

BACKGROUND OF THE INVENTION

Field of the Invention

The invention belongs to the field of medicine, specifically relates to an ophthalmic pharmaceutical composition, and also relates to an ophthalmic kit and medical application thereof.

Description of Related Art

Anatomically, the eyeball includes two parts, anterior and posterior segments of eyeball, wherein the anterior segment of eyeball accounts for approximately ⅓ and is composed of cornea, pupil, iris, aqueous humor, ciliary body and lens, while the posterior segment of eyeball accounts for approximately ⅔ and is composed of vitreum, retina, macula lutea, optic nerve, choroid and sclera. Abnormalities in any part of the eyeball may cause eye diseases, wherein eye diseases such as retinal phlebitis, diabetic retinopathy, proliferative vitreoretinopathy, choroidal neovascularization, age-related macular degeneration, macular cystoid edema, vitreous macular adhesion, macular hole are the main causes of visual impairments. At present, ocular surface administration and systemic administration are still the main modes of administration for the treatment of diseases in the posterior segment of eyeball. However, due to the presence of tear barrier, corneal barrier, and conjunctival barrier, the ocular surface administration is difficult to reach the posterior segment of eyeball; in addition, due to the effects of blood-aqueous humor and blood-retina barriers, the systemic administration requires large dose and multiple administrations in order to make the amount of drug reaching the posterior segment of eyeball meet the therapeutic need. Based on this situation, in order to increase the amount of drug reaching the posterior segment of eyeball, periocular injection and intravitreal injection are gradually adopted; however, most drugs have a short half-life in vitreum, which requires multiple injections to maintain the amount of drug in vitreum to meet the treatment requirements, which causes pain to patients, reduces patient compliance, and increases the risk of intraocular infections.

In order to solve the problems caused by multiple injections, sustained-release implants have been clinically used to treat diseases in the posterior segment of eyeball. The sustained-release implants are classified into non-biodegradable and biodegradable types according to materials. For example, Vitrasert, a ganciclovir implant developed by Australian company pSivida for the treatment of cytomegalovirus retinitis and approved by the FDA in 1996, uses non-biodegradable materials polyvinyl alcohol and ethylene-vinyl acetate copolymer as release-controlling material. In 2005, Retisert, a fluocinonide implant developed by the same company mainly for the treatment of non-infective uveitis was approved by the FDA. Retisert uses non-biodegradable materials polyvinyl alcohol and silicone oil as release-controlling materials. Since non-biodegradable sustained-release implants cannot be degraded, they need to be removed through secondary surgery. In order to solve this problem, biodegradable implants are developed. Commonly used biodegradable sustained-release materials include hypromellose, polylactic acid, polyglycolic acid, and polylactic acid-co-glycolic acid copolymer, and representative products in the market are Surodex and Ozurdex of Allergancompany, in which the former uses polylactic acid-co-glycolic acid copolymer and hypromellose as materials to prepare a dexamethasone implant, and can continuously release dexamethasone for 7 to 10 days for the treatment of anti-inflammatory after cataract surgery, while the latter uses polylactic acid-co-glycolic acid copolymer as material to prepare a dexamethasone implant for the treatment of macular edema and uveitis. However, both of the non-biodegradable implants and the biodegradable implants currently need to be implanted into the eye through surgery or special drug delivery devices (for example, Ozurdex is equipped with a special injection device). The operation is more complicated and brings some pains to patients.

There is currently a need for an ophthalmic drug that is simple in administration and has a sustained-release effect.

SUMMARY OF THE INVENTION

The present invention provides an ophthalmic pharmaceutical composition, which can be injected into an eye by injection. The ophthalmic pharmaceutical composition of the present invention can slowly release an active pharmaceutical ingredient in the eye for a long time and can be degraded in the eye. Based on this, the present invention also provides an ophthalmic kit and medical use thereof.

A first aspect of the present invention relates to an ophthalmic pharmaceutical composition, comprising the following components:

a solid matrix: 0.06 to 40 parts by weight (e.g. 0.08 parts by weight, 0.1 parts by weight, 0.3 parts by weight, 0.5 parts by weight, 0.7 parts by weight, 0.8 parts by weight, 1 part by weight, 1.3 parts by weight, 1.6 parts by weight, 1.8 parts by weight, 2 parts by weight, 2.5 parts by weight, 3 parts by weight, 4 parts by weight, 6 parts by weight, 8 parts by weight, 10 parts by weight, 13 parts by weight, 15 parts by weight, 17 parts by weight, 20 parts by weight, 22 parts by weight, 25 parts by weight, 27 parts by weight, 30 parts by weight, 33 parts by weight, 36 parts by weight, 38 parts by weight, 37 parts by weight)

a liquid matrix: 0.4 to 55 parts by weight (e.g. 0.8 parts by weight, 1 part by weight, 1.5 parts by weight, 2 parts by weight, 2.3 parts by weight, 2.5 parts by weight, 2.8 parts by weight, 3 parts by weight, 3.5 parts by weight, 4 parts by weight, 4.6 parts by weight, 5 parts by weight, 7 parts by weight, 8 parts by weight, 10 parts by weight, 12 parts by weight, 14 parts by weight, 16 parts by weight, 20 parts by weight, 22 parts by weight, 24 parts by weight, 26 parts by weight, 28 parts by weight, 30 parts by weight, 34 parts by weight, 38 parts by weight, 40 parts by weight, 45 parts by weight, 47 parts by weight)

an active pharmaceutical ingredient: 1 part by weight;

in which, the solid matrix is at least one selected from the group consisting of polylactic acid, polyglycolic acid, polylactic acid-co-glycolic acid copolymer, and polyethylene glycol having a number average molecular weight of 800 to 10,000 (e.g., 1800 to 2200, 900, 1000, 1200, 1400, 1600, 2000, 2800, 3000, 5000, 7000, 8000, 9500, 9000);

the liquid matrix is a first liquid matrix and/or a second liquid matrix;

the first liquid matrix is at least one selected from the group consisting of diethyl succinate, diethyl tartrate, dimethyl glutarate, and glycerol triacetate;

when the liquid matrix is the first liquid matrix and the second liquid matrix, the second liquid matrix is at least one selected from the group consisting of glycerol, propylene glycol, and polyethylene glycol having a number average molecular weight of 70 to 750 (e.g., 190 to 210, 300, 380 to 420, 570 to 630, 100, 200, 400, 500, 600, 700);

when the liquid matrix is the second liquid matrix, the second liquid matrix is glycerol and/or propylene glycol, or a combination of polyethylene glycol having a number average molecular weight of 70 to 750 (e.g., 190 to 210, 300, 380 to 420, 570 to 630, 100, 200, 400, 500, 600, 700) and at least one selected from the group consisting of glycerol and propylene glycol.

In some embodiments of the first aspect of the present invention, the second liquid matrix is glycerol and/or propylene glycol, or a mixture of polyethylene glycol having a number average molecular weight of 70 to 750 (e.g., 190 to 210, 300, 380 to 420, 570 to 630, 100, 200, 400, 500, 600, 700) and at least one selected from the group consisting of glycerol and propylene glycol.

In some embodiments of the first aspect of the present invention, the second liquid matrix is glycerol and/or propylene glycol.

In some embodiments of the first aspect of the present invention, the second liquid matrix is a combination of polyethylene glycol having a number average molecular weight of 70 to 750 (e.g., 190 to 210, 300, 380 to 420, 570 to 630, 100, 200, 400, 500, 600, 700) and at least one selected from the group consisting of glycerol and propylene glycol.

In some embodiments of the first aspect of the present invention, the second liquid matrix is a mixture of polyethylene glycol having a number average molecular weight of 70 to 750 (e.g., 190 to 210, 300, 380 to 420, 570 to 630, 100, 200, 400, 500, 600, 700) and at least one selected from the group consisting of glycerol and propylene glycol.

In some embodiments of the first aspect of the present invention, the second liquid matrix is polyethylene glycol having a number average molecular weight of 70 to 750 (for example, 190 to 210, 300, 380 to 420, 570 to 630, 100, 200, 400, 500, 600, 700) and glycerol.

In some embodiments of the first aspect of the present invention, the second liquid matrix is polyethylene glycol having a number average molecular weight of 70 to 750 (for example, 190 to 210, 300, 380 to 420, 570 to 630, 100, 200, 400, 500, 600, 700) and propylene glycol.

In some embodiments of the first aspect of the present invention, the second liquid matrix is polyethylene glycol having a number average molecular weight of 70 to 750 (for example, 190 to 210, 300, 380 to 420, 570 to 630, 100, 200, 400, 500, 600, 700), glycerol, and propylene glycol.

In some embodiments of the first aspect of the present invention, the polylactic acid has a weight average molecular weight of 1,000 to 500,000, for example, 3,000 to 60,000, 6000, 8000, 9000, 10,000, 40,000, 60,000, 80,000, 100,000, 200,000, 300,000, 400,000, and 450,000.

In some embodiments of the first aspect of the present invention, the polyglycolic acid has a weight average molecular weight of 1,000 to 600,000, for example, 5000 to 50,000, 3000, 4000, 6000, 8000, 10,000, 30,000, 50,000, 100,000, 200,000, 300,000, and 500,000.

In some embodiments of the first aspect of the present invention, the polylactic acid-co-glycolic acid copolymer has a weight average molecular weight of 1,000 to 500,000, for example, 5,000 to 50,000, 3000, 4000, 6000, 8000, 9000, 10,000, 40,000, 60,000, 80,000, 100,000, 200,000, 300,000, 400,000, and 450,000.

In the present invention, the number average molecular weight is measured according to a conventional method, such as an end-group analysis method, a boiling point elevation method, a freezing point reduction method, a vapor pressure osmosis method, and a thin film osmosis method.

In the present invention, the weight average molecular weight is measured according to a conventional method, such as a light scattering method, a gel chromatography method, an ultracentrifugal sedimentation rate method, and a small-angle X-ray diffraction method.

Some embodiments of the first aspect of the present invention comprise any one of the following items A to F:

A. the ophthalmic pharmaceutical composition comprises the following components:

a solid matrix: 0.08 to 30 parts by weight (e.g., 0.1 parts by weight, 0.3 parts by weight, 0.5 parts by weight, 0.7 parts by weight, 0.8 parts by weight, 1 part by weight, 1.3 parts by weight, 1.6 parts by weight, 1.8 parts by weight, 2 parts by weight, 2.5 parts by weight, 3 parts by weight, 4 parts by weight, 6 parts by weight, 8 parts by weight, 10 parts by weight, 13 parts by weight, 15 parts by weight, 17 parts by weight, 20 parts by weight, 22 parts by weight, 25 parts by weight, 27 parts by weight)

a first liquid matrix: 0.8 to 40 parts by weight (e.g., 1 part by weight, 1.5 parts by weight, 2 parts by weight, 2.3 parts by weight, 2.5 parts by weight, 2.8 parts by weight, 3 parts by weight, 3.5 parts by weight, 4 parts by weight, 4.6 parts by weight, 5 parts by weight, 7 parts by weight, 8 parts by weight, 10 parts by weight, 12 parts by weight, 14 parts by weight, 16 parts by weight, 20 parts by weight, 22 parts by weight, 24 parts by weight, 26 parts by weight, 28 parts by weight, 30 parts by weight, 34 parts by weight, 38 parts by weight)

an active pharmaceutical ingredient: 1 part by weight;

B. the ophthalmic pharmaceutical composition comprises the following components:

a solid matrix: 0.08 to 14 parts by weight (e.g., 0.1 parts by weight, 0.2 parts by weight, 0.3 parts by weight, 0.5 parts by weight, 0.7 parts by weight, 0.8 parts by weight, 1 part by weight, 1.3 parts by weight, 1.6 parts by weight, 1.8 parts by weight, 2 parts by weight, 2.5 parts by weight, 3 parts by weight, 4 parts by weight, 6 parts by weight, 8 parts by weight, 10 parts by weight, 13 parts by weight)

a first liquid matrix: 0.8 to 20 parts by weight (e.g., 1 part by weight, 1.5 parts by weight, 2 parts by weight, 2.3 parts by weight, 2.5 parts by weight, 2.8 parts by weight, 3 parts by weight, 3.5 parts by weight, 4 parts by weight, 4.6 parts by weight, 5 parts by weight, 7 parts by weight, 8 parts by weight, 10 parts by weight, 12 parts by weight, 14 parts by weight, 16 parts by weight, 20 parts by weight)

a second liquid matrix: 0.1 to 18 parts by weight (e.g., 0.2 parts by weight, 0.15 parts by weight, 0.25 parts by weight, 0.3 parts by weight, 0.33 parts by weight, 0.37 parts by weight, 0.4 parts by weight, 1 part by weight, 2 parts by weight, 3 parts by weight, 4 parts by weight, 5 parts by weight, 6 parts by weight, 7 parts by weight, 8 parts by weight, 9 parts by weight, 10 parts by weight, 12 parts by weight, 13 parts by weight, 15 parts by weight, 16 parts by weight, 17 parts by weight, 18 parts by weight)

an active pharmaceutical ingredient: 1 part by weight;

C. the ophthalmic pharmaceutical composition comprises the following components:
- a solid matrix: 0.8 to 20 parts by weight (e.g. 1 part by weight, 1.2 parts by weight, 1.3 parts by weight, 1.5 parts by weight, 1.6 parts by weight, 1.7 parts by weight, 1.9 parts by weight, 2 parts by weight, 2.2 parts by weight, 2.5 parts by weight, 3 parts by weight, 4 parts by weight, 5 parts by weight, 6 parts by weight, 7 parts by weight, 9 parts by weight, 1 part by weight, 13 parts by weight, 15 parts by weight, 17 parts by weight, 18 parts by weight, 19 parts by weight)
- a second liquid matrix: 0.7 to 40 parts by weight (e.g., 0.9 parts by weight, 1 part by weight, 1.1 parts by weight, 1.2 parts by weight, 1.25 parts by weight, 2 parts by weight, 3 parts by weight, 4 parts by weight, 5 parts by weight, 7 parts by weight, 9 parts by weight, 10 parts by weight, 13 parts by weight, 15 parts by weight, 17 parts by weight, 18 parts by weight, 20 parts by weight, 22 parts by weight, 24 parts by weight, 26 parts by weight, 29 parts by weight, 30 parts by weight, 32 parts by weight Parts by weight, 35 parts by weight, 36 parts by weight, 37 parts by weight, 39 parts by weight)
- an active pharmaceutical ingredient: 1 part by weight;

D. the ophthalmic pharmaceutical composition comprises the following components:
- polylactic acid-co-glycolic acid copolymer: 0.08 to 26 parts by weight (e.g., 0.1 parts by weight, 0.3 parts by weight, 0.5 parts by weight, 0.7 parts by weight, 0.8 parts by weight, 1 part by weight, 1.3 parts by weight, 1.6 parts by weight, 1.8 parts by weight, 2 parts by weight, 2.5 parts by weight, 3 parts by weight, 4 parts by weight, 6 parts by weight, 8 parts by weight, 10 parts by weight, 13 parts by weight, 15 parts by weight, 17 parts by weight, 20 parts by weight, 22 parts by weight, 25 parts by weight)
- a first liquid matrix: 0.8 to 37 parts by weight (e.g., 1 part by weight, 1.5 parts by weight, 2 parts by weight, 2.3 parts by weight, 2.5 parts by weight, 2.8 parts by weight, 3 parts by weight, 3.5 parts by weight, 4 parts by weight, 4.6 parts by weight, 5 parts by weight, 7 parts by weight, 8 parts by weight, 10 parts by weight, 12 parts by weight, 14 parts by weight, 16 parts by weight, 20 parts by weight, 22 parts by weight, 24 parts by weight, 26 parts by weight, 28 parts by weight, 30 parts by weight, 34 parts by weight)
- an active pharmaceutical ingredient: 1 part by weight;
- preferably, the first liquid matrix is diethyl succinate, diethyl tartrate, dimethyl glutarate or glycerol triacetate;
- preferably, the mass ratio of polylactic acid to glycolic acid in the polylactic acid-co-glycolic acid copolymer is 1:(1 to 5), such as 1:2, 1:3, 1:4;

E. the ophthalmic pharmaceutical composition comprises the following components:
- polylactic acid-co-glycolic acid copolymer: 0.08 to 10 parts by weight (e.g., 0.1 parts by weight, 0.2 parts by weight, 0.3 parts by weight, 0.5 parts by weight, 0.7 parts by weight, 0.8 parts by weight, 1 part by weight, 1.3 parts by weight, 1.6 parts by weight, 1.8 parts by weight, 2 parts by weight, 2.5 parts by weight, 3 parts by weight, 4 parts by weight, 6 parts by weight, 8 parts by weight)
- a first liquid matrix: 0.8 to 18 parts by weight (e.g., 1 part by weight, 1.5 parts by weight, 2 parts by weight, 2.3 parts by weight, 2.5 parts by weight, 2.8 parts by weight, 3 parts by weight, 3.5 parts by weight, 4 parts by weight, 4.6 parts by weight, 5 parts by weight, 7 parts by weight, 8 parts by weight, 10 parts by weight, 12 parts by weight, 14 parts by weight, 16 parts by weight)
- polyethylene glycol having a number average molecular weight of 70 to 750:0.1 to 16 parts by weight (e.g., 0.2 parts by weight, 0.15 parts by weight, 0.25 parts by weight, 0.3 parts by weight, 0.33 parts by weight, 0.37 parts by weight, 0.4 parts by weight, 1 part by weight, 2 parts by weight, 3 parts by weight, 4 parts by weight, 5 parts by weight, 6 parts by weight, 7 parts by weight, 8 parts by weight, 9 parts by weight, 10 parts by weight, 12 parts by weight, 13 parts by weight, 15 parts by weight)
- an active pharmaceutical ingredient: 1 part by weight;
- preferably, the first liquid matrix is diethyl succinate, diethyl tartrate, dimethyl glutarate or glycerol triacetate;
- preferably, the mass ratio of polylactic acid to glycolic acid in the polylactic acid-co-glycolic acid copolymer is 1:(1 to 5), such as 1:2, 1:3, 1:4;

F. the ophthalmic pharmaceutical composition comprises the following components:
- a solid matrix: 0.8-15 parts by weight (e.g. 1 part by weight, 1.2 parts by weight, 1.3 parts by weight, 1.5 parts by weight, 1.6 parts by weight, 1.7 parts by weight, 1.9 parts by weight, 2 parts by weight, 2.2 parts by weight, 2.5 parts by weight, 3 parts by weight, 4 parts by weight, 5 parts by weight, 6 parts by weight, 7 parts by weight, 9 parts by weight, 1 part by weight, 13 parts by weight)
- a second liquid matrix: 0.7 to 20 parts by weight (e.g., 0.9 parts by weight, 1 part by weight, 1.1 parts by weight, 1.2 parts by weight, 1.25 parts by weight, 2 parts by weight, 3 parts by weight, 4 parts by weight, 5 parts by weight, 7 parts by weight, 9 parts by weight, 10 parts by weight, 13 parts by weight, 15 parts by weight, 17 parts by weight, 18 parts by weight)
- an active pharmaceutical ingredient: 1 part by weight;
- preferably, the solid matrix is polylactic acid, polyglycolic acid, polylactic acid-co-glycolic acid copolymer, or polyethylene glycol having a number average molecular weight of 800 to 10,000 (e.g., 1800 to 2200, 900, 1000, 1200, 1400, 1600, 2000, 2800, 3000, 5000, 7000, 8000, 9500, 9000).

In some embodiments of the first aspect of the present invention, the active pharmaceutical ingredient is at least one selected from the group consisting of an anti-tumor drug, an anti-inflammatory drug, an immunosuppressive agent, an agiogenesis inhibitor, and a glaucoma treatment drug.

In some embodiments of the first aspect of the present invention, the active pharmaceutical ingredient is at least one selected from the group consisting of chlorambucil, melphmike, cyclophosphamide, ifosfamide, carmustine, lomustine, semustine, chlorozotocin, cisplatin, carboplatin, oxaliplatin, fluorouracil, mitoxantrone, irinotecan, topotecan, vinblastine, vincristine, vindesine, vinorelbine, etoposide, teniposide, paclitaxel, docetaxel, bleomycin, methotrexate, gemcitabine, capecitabine, hydroxyurea, mitomycin, gefitinib, sunitinib, dexamethasone, dexamethasone acetate, prednisone, prednisone acetate, fluocinolone, fluocinolone acetate, triamcinolone acetonide, methylprednisolone, methylprednisolone aceponate, halobetasol propionate, cortisone, hydrocortisone, cyclosporine, rapamycin, tacrolimus, mycophenolate mofetil, fujimycin, mizoribine, sulfasalazine, azathioprine, methotrexate, bevacizumab, ranibizumab, pegaptanib sodium, aflibercept, latanoprost, travoprost, Bi-matoprost, bimatoprost, tafluprost, pilocarpine, atropine, scopolamine, betaxolol, metoprolol, bunolol, metipranolol, propranolol, timolol, befunolol, acetazolamide, dorzolamide, brinzolamide, apraclonidine, brimonidine, dipivefrine, guanethidine, dapiprazole, dasatinib, and pharmaceutically acceptable salts thereof.

In some embodiments of the first aspect of the present invention, the active pharmaceutical ingredient is at least one selected from the group consisting of dexamethasone, latanoprost, dasatinib, triamcinolone acetonide, and pharmaceutically acceptable salts thereof.

In some embodiments of the first aspect of the present invention, the ophthalmic pharmaceutical composition is an ophthalmic pharmaceutical preparation, preferably an ophthalmic pharmaceutical injection preparation.

In the present invention, the anti-tumor drugs include, but are not limited to, chlorambucil, meloxicam, cyclophosphamide, ifosfamide, carmustine, lomustine, semustine, chlorozotocin, cisplatin, carboplatin, oxaliplatin, fluorouracil, mitoxantrone, irinotecan, topotecan, vinblastine, vincristine, vindesine, vinorelbine, etoposide, teniposide, paclitaxel, docetaxel, bleomycin, methotrexate, gemcitabine, capecitabine, hydroxyurca, mitomycin, gefitinib, sunitinib.

In the present invention, the anti-inflammatory drugs include, but are not limited to, dexamethasone, dexamethasone acetate, prednisone, prednisone acetate, fluocinolone, fluocinolone acetate, triamcinolone acetonide, methylprednisolone, methylprednisolone aceponate, halobetasol propionate, cortisone, hydrocortisone.

In the present invention, the immunosuppressive agents include, but are not limited to, cyclosporine, rapamycin, tacrolimus, mycophenolate mofetil, fujimycin, mizoribine, sulfasalazine, azathioprine, methotrexate.

In the present invention, the agiogenesis inhibitors include, but are not limited to, bevacizumab, ranibizumab, pegaptanib sodium, and aflibercept.

In the present invention, the glaucoma treatment drugs include, but are not limited to, latanoprost, travoprost, Bi-matoprost, bimatoprost, tafluprost, pilocarpine, atropine, scopolamine, betaxolol, metoprolol, bunolol, metipranolol, propranolol, timolol, befunolol, acetazolamide, dorzolamide, brinzolamide, apraclonidine, brimonidine, dipivefrine, guanethidine, dapiprazole.

A second aspect of the present invention relates to a method for preparing the ophthalmic pharmaceutical composition according to the first aspect of the present invention, comprising the following steps:
(1) mixing the solid matrix with the liquid matrix to obtain a mixed substance;
(2) mixing the mixed substance obtained in step (1) with the active pharmaceutical ingredient.

In some embodiments of the second aspect of the present invention, in step (1), the mixing is performed at a temperature of 20° C. to 100° C., such as 30° C., 4° C., 45° C., 50° C., 55° C., 60° C., 65° C., 70° C., 75° C., 80° C., 85° C., 90° C., 95° C.

In some embodiments of the second aspect of the present invention, the solid matrix and the liquid matrix is mixed at a mass ratio of (0.06~ 40):(0.4~ 55), preferably (0.08~ 30):(0.8~40), more preferably (0.1~ 20):(1~ 30).

In some embodiments of the second aspect of the present invention, the mass ratio of the solid matrix to the active pharmaceutical ingredient is (0.06~ 40): 1, preferably (0.08~ 30): 1, and more preferably (0.1~ 20): 1.

A third aspect of the present invention relates to an ophthalmic kit, comprising: a solid matrix, a liquid matrix, and an active pharmaceutical ingredient;
wherein,
the solid matrix is at least one selected from the group consisting of polylactic acid, polyglycolic acid, polylactic acid-co-glycolic acid copolymer, and polyethylene glycol having a number average molecular weight of 800 to 10,000 (e.g., 1800 to 2200, 900, 1000, 1200, 1400, 1600, 2000, 2800, 3000, 5000, 7000, 8000, 9500, 9000);
the liquid matrix is a first liquid matrix and/or a second liquid matrix;
the first liquid matrix is at least one selected from the group consisting of diethyl succinate, diethyl tartrate, dimethyl glutarate, and glycerol triacetate;
when the liquid matrix is the first liquid matrix and the second liquid matrix, the second liquid matrix is at least one selected from glycerol, propylene glycol and polyethylene glycol having a number average molecular weight of 70 to 750 (e.g., 190 to 210, 300, 380 to 420, 570 to 630, 100, 200, 400, 500, 600, 700);
when the liquid matrix is the second liquid matrix, the second liquid matrix is glycerol and/or propylene glycol, or a combination of polyethylene glycol having a number average molecular weight of 70 to 750 (e.g., 190 to 210, 300, 380 to 420, 570 to 630, 100, 200, 400, 500, 600, 700) and at least one selected from glycerol and propylene glycol.

In some embodiments of the third aspect of the present invention, the ophthalmic kit characterized in one or more of the following items i to iii:
i. the ophthalmic kit further comprises a syringe (such as a medical syringe);
ii. the ophthalmic kit is an ophthalmic injection kit;
iii. the active pharmaceutical ingredient is at least one selected from the group consisting of an antitumor drug, an anti-inflammatory drug, an immunosuppressive agent, an agiogenesis inhibitor, and a glaucoma treatment drug;
preferably, the active pharmaceutical ingredient is at least one selected from the group consisting of chlorambucil, melphmike, cyclophosphamide, ifosfamide, carmustine, lomustine, semustine, chlorozotocin, cisplatin, carboplatin, oxaliplatin, fluorouracil, mitoxantrone, irinotecan, topotecan, vinblastine, vincristine, vindesine, vinorelbine, etoposide, teniposide, paclitaxel, docetaxel, bleomycin, methotrexate, gemcitabine, capecitabine, hydroxyurea, mitomycin, gefitinib, sunitinib, dexamethasone, dexamethasone acetate, prednisone, prednisone acetate, fluocinolone, fluocinolone acetate, triamcinolone acetonide, methylprednisolone, methylprednisolone aceponate, halobetasol propionate, cortisone, hydrocortisone, cyclosporine, rapamycin, tacrolimus, mycophenolate mofetil, fujimycin, mizoribine, sulfasalazine, azathioprine, methotrexate, bevacizumab, ranibizumab, pegaptanib sodium, aflibercept, latanoprost, travoprost, Bi-matoprost, bimatoprost, tafluprost, pilocarpine, atropine, scopolamine, betaxolol, metoprolol, bunolol, metipranolol, propranolol, timolol, befunolol, acetazolamide, dorzolamide, brinzolamide, apraclonidine, brimonidine, dipivefrine, guanethidine, dapiprazole, dasatinib, and pharmaceutically acceptable salts thereof;

more preferably, the active pharmaceutical ingredient is at least one selected from the group consisting of dexamethasone, latanoprost, dasatinib, triamcinolone acetonide, and pharmaceutically acceptable salts thereof.

A fourth aspect of the present invention relates to an ophthalmic sustained-release medicament, which comprises the ophthalmic pharmaceutical composition according to the first aspect of the present invention or the ophthalmic kit according to the third aspect of the present invention;

preferably, the ophthalmic sustained-release medicament is a sustained-release medicament for ophthalmic injection.

A fifth aspect of the present invention relates to use of the ophthalmic pharmaceutical composition according to the first aspect of the present invention, the ophthalmic kit according to the third aspect of the present invention, or the ophthalmic sustained-release medicament according to the fourth aspect of the present invention in manufacture of a medicament for the prevention and/or treatment of an eye disease.

In some embodiments of the fifth aspect of the present invention, the eye disease is a disease of posterior segment of the eyeball.

In some embodiments of the fifth aspect of the present invention, the eye disease is at least one selected from the group consisting of cataract postoperative inflammation, glaucoma, uveitis, retinal vein occlusion, retinal artery occlusion, diabetic retinopathy, retinal phlebitis, proliferative vitroretinopathy, choroidal neovascularization, cystoid macular edema, age-related macular degeneration, vitreous macular adhesion, macular hole, optic neuritis, optic disc edema, optic nerve meningioma, optic nerve gliomas, retinoblastoma and choroidoblastoma.

A sixth aspect of the present invention relates to a method for preventing and/or treating an eye disease, comprising a step of injecting the ophthalmic pharmaceutical composition according to the first aspect of the present invention or the ophthalmic sustained-release medicament according to the fourth aspect of the present invention into an eye.

In some embodiments of the sixth aspect of the present invention, the eye disease is a disease of posterior segment of the eyeball.

In some embodiments of the sixth aspect of the present invention, the eye disease is at least one selected from the group consisting of cataract postoperative inflammation, glaucoma, uveitis, retinal vein occlusion, retinal artery occlusion, diabetic retinopathy, retinal phlebitis, proliferative vitroretinopathy, choroidal neovascularization, cystoid macular edema, age-related macular degeneration, vitreous macular adhesion, macular hole, optic neuritis, optic disc edema, optic nerve meningioma, optic nerve gliomas, retinoblastoma and choroidoblastoma.

In some embodiments of the sixth aspect of the invention, the injecting is performed into a posterior segment of the eyeball.

The present invention also relates to the ophthalmic pharmaceutical composition according to the first aspect of the present invention, the ophthalmic kit according to the third aspect, or the ophthalmic sustained-release medicament according to the fourth aspect for use in preventing and/or treating an eye disease;

preferably, the eye disease is a disease of posterior segment of the eyeball;

preferably, the eye disease is at least one selected from the group consisting of cataract postoperative inflammation, glaucoma, uveitis, retinal vein occlusion, retinal artery occlusion, diabetic retinopathy, retinal phlebitis, proliferative vitroretinopathy, choroidal neovascularization, cystoid macular edema, age-related macular degeneration, vitreous macular adhesion, macular hole, optic neuritis, optic disc edema, optic nerve meningioma, optic nerve gliomas, retinoblastoma and choroidoblastoma.

The present invention also relates to the following aspects:

1. An ophthalmic sustained-release drug delivery system, characterized in being consisted of the following components:
   (1) a liquid matrix having a biocompatibility,
   (2) a solid matrix having a biocompatibility, and
   (3) a drug, wherein the liquid matrix is one or a mixture of more than one of diethyl succinate, diethyl tartrate, dimethyl glutarate, glycerol triacetate, polyethylene glycol, glycerol, and propylene glycol; the solid matrix is one or a mixture of more than one of polyethylene glycol, polylactic acid, polyglycolic acid, and polylactic acid-co-glycolic acid copolymer;
   the weight ratio of the drug, the liquid matrix, and the solid matrix is 1:(0.1-45):(0.1-99).

2. The ophthalmic sustained-release drug delivery system according to Aspect 1, characterized in that the weight ratio of the drug, the liquid matrix, and the solid matrix is 1:(1-20):(0.1-10).

3. The ophthalmic sustained-release drug delivery system according to Aspect 2, characterized in that the weight ratio of the drug, the liquid matrix, and the solid matrix is 1:(1-5):(0.1-2).

4. The ophthalmic sustained-release drug delivery system according to Aspect 1, characterized in that the liquid matrix in (1) is a mixture of more than one of diethyl succinate, diethyl tartrate, dimethyl glutarate, glycerol triacetate, polyethylene glycol, glycerol and propylene glycol, or one or a mixture of more than one of diethyl succinate, diethyl tartrate, dimethyl glutarate and glycerol triacetate.

5. The ophthalmic sustained-release drug delivery system according to Aspect 4, characterized in that the polyethylene glycol in the liquid matrix is one or a mixture of more than one of PEG-200, PEG-300, PEG-400 and PEG-600.

6. The ophthalmic sustained-release drug delivery system according to Aspect 4, characterized in that the polyethylene glycol in the liquid matrix is PEG-400.

7. The ophthalmic sustained-release drug delivery system according to Aspect 1, characterized in that the polyethylene glycol in the solid matrix in (2) is one or a mixture of more than one of PEG-800, PEG-1000, PEG-1500, PEG-2000, PEG-4000, PEG-6000, PEG-8000, PEG-10000 and PEG-20000.

8. The ophthalmic sustained-release drug delivery system according to Aspect 1, characterized in that the solid matrix is polylactic acid-co-glycolic acid copolymer.

9. The ophthalmic sustained-release drug delivery system according to Aspect 1, characterized in being consisted of the following components:
   (1) a liquid matrix having a biocompatibility, wherein the liquid matrix is one or a mixture of more than one of diethyl succinate, diethyl tartrate, dimethyl glutarate, glycerol triacetate, polyethylene glycol, glycerol, and propylene glycol;
   (2) a polylactic acid-co-glycolic acid copolymer; and (3) a drug, wherein the drug is an anti-tumor drug, an anti-inflammatory drug, an immunosuppressive agent, an agiogenesis inhibitor, or a glaucoma treatment drug; the weight ratio of the drug, the liquid matrix, and the polylactic acid-co-glycolic acid copolymer is 1:(1-2): (0.1-2).

10. An ophthalmic sustained-release drug delivery system of Aspect 1, wherein the drug is an anti-tumor drug, an anti-inflammatory drug, an immunosuppressive agent, an agiogenesis inhibitor, or a glaucoma treatment drug.

In the present invention, unless otherwise specified,

The term "matrix" refers to a substance that does not react with the active pharmaceutical ingredient and is conducive to play the role of the active pharmaceutical ingredient, for example, a substance having effects on administration, release, penetration and absorption of the active pharmaceutical ingredient, a substance capable of shaping the active pharmaceutical ingredient, etc.

The term "liquid matrix" refers to a matrix that is liquid at ordinary temperatures.

The term "solid matrix" refers to a matrix that is solid at ordinary temperatures.

The present invention achieves at least one of the following beneficial effects:

1. The ophthalmic pharmaceutical composition of the present invention can be injected into the eye by injection, and can continuously and slowly release the active pharmaceutical ingredient in the eye.

2. The ophthalmic pharmaceutical composition of the present invention can be degraded in the eye.

3. The stability of the ophthalmic pharmaceutical composition of the present invention is good.

4. The ophthalmic kit of the present invention can be used to prepare a medicament on site for use, thereby extending the shelf life of the medicament.

BRIEF DESCRIPTION OF THE DRAWINGS

The drawings described here are used to provide a further understanding of the present invention and constitute a part of the present application. The schematic examples of the present invention and the descriptions thereof are used to explain the present invention and do not constitute an improper limitation on the present invention. In the drawings.

DESCRIPTION OF THE INVENTION

Figure 1:
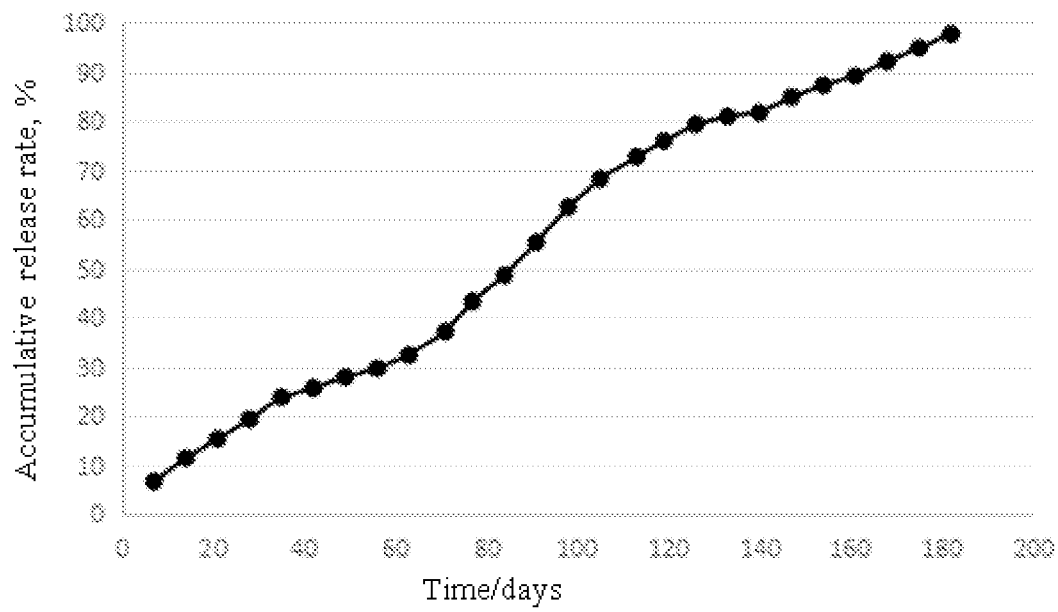
FIG. 1 shows a schematic diagram of in vitro release rate of the ophthalmic preparation 36 in Experimental Example 3.
Figure 2:
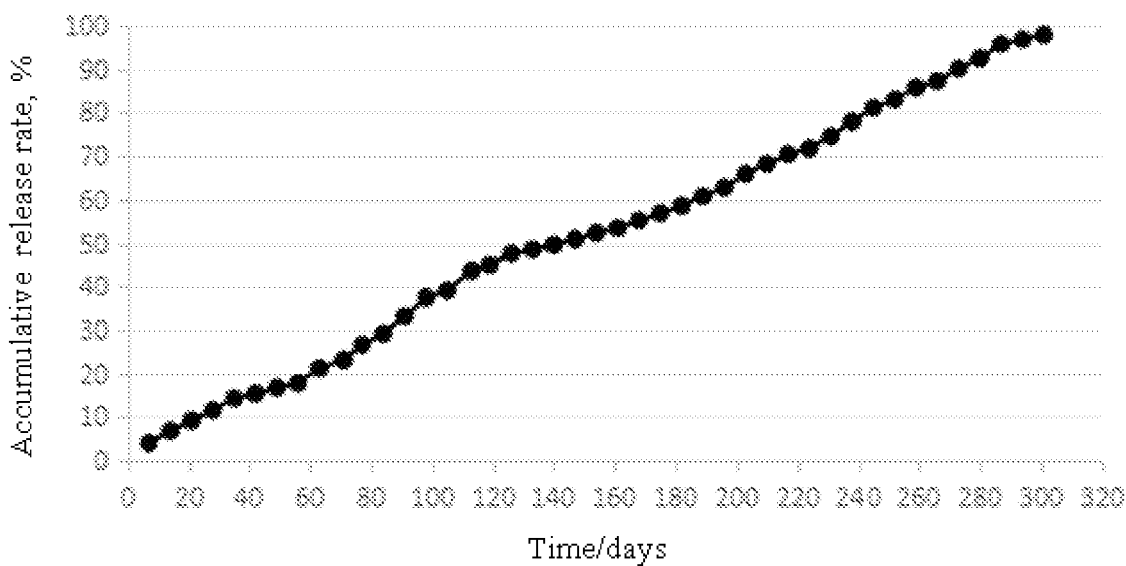
FIG. 2 shows a schematic diagram of in vitro release rate of the ophthalmic preparation 37 in Experimental Example 3.
Figure 3:
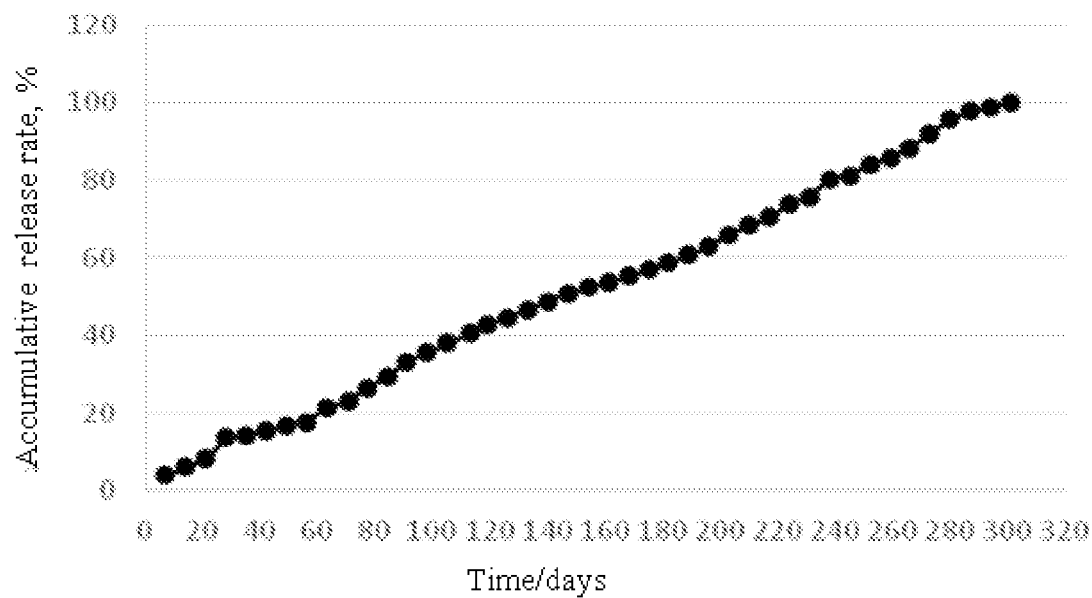
FIG. 3 shows a schematic diagram of in vitro release rate of the ophthalmic preparation 38 in Experimental Example 3.
Figure 4:
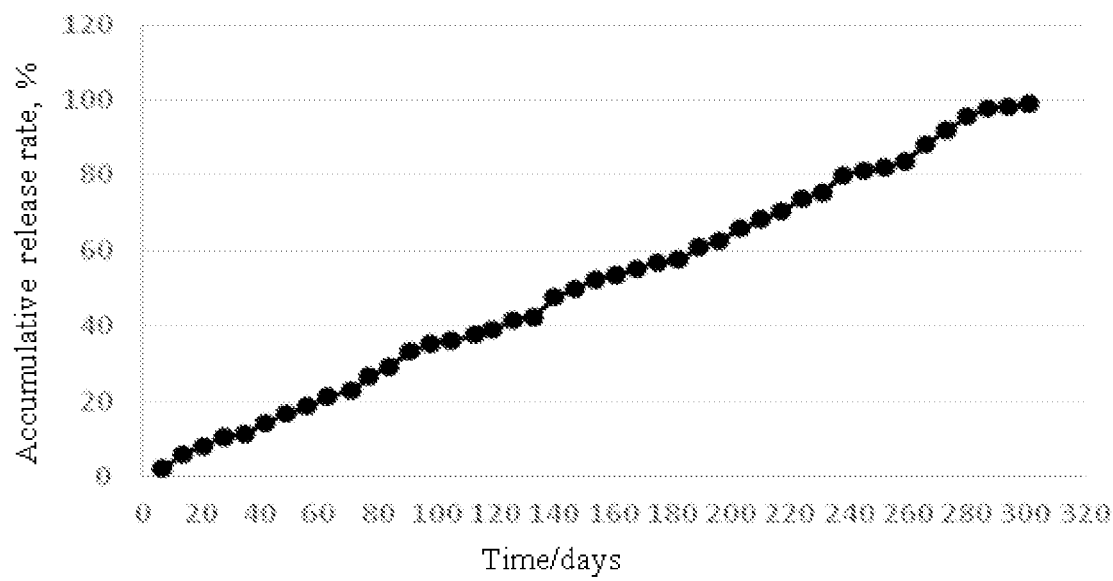
FIG. 4 shows a schematic diagram of in vitro release rate of the ophthalmic preparation 39 in Experimental Example 3.
Figure 5:
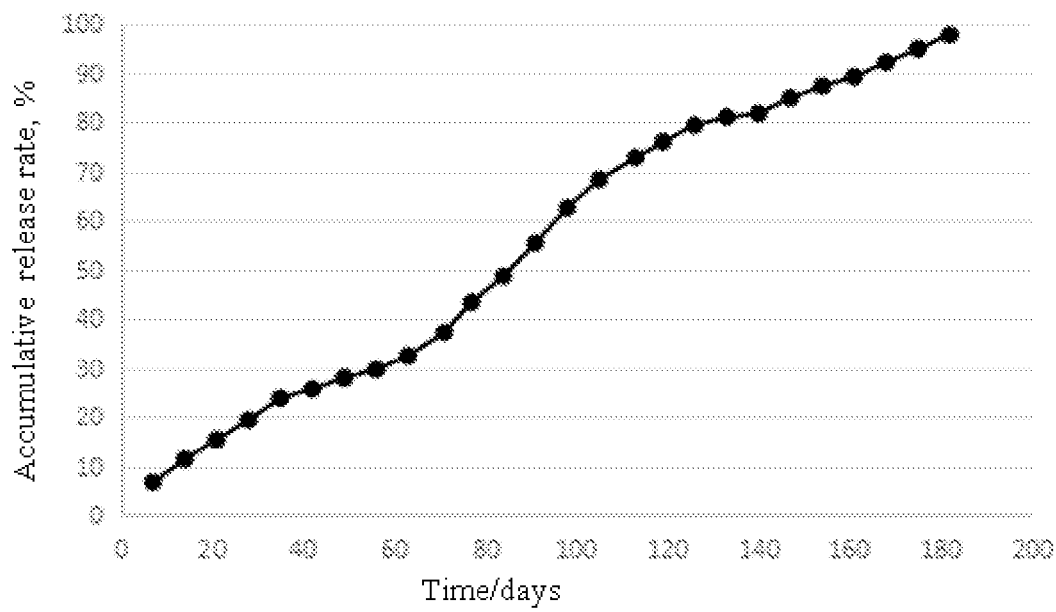
FIG. 5 shows a schematic diagram of in vitro release rate of the ophthalmic preparation 24 in Experimental Example 3.
Figure 6:
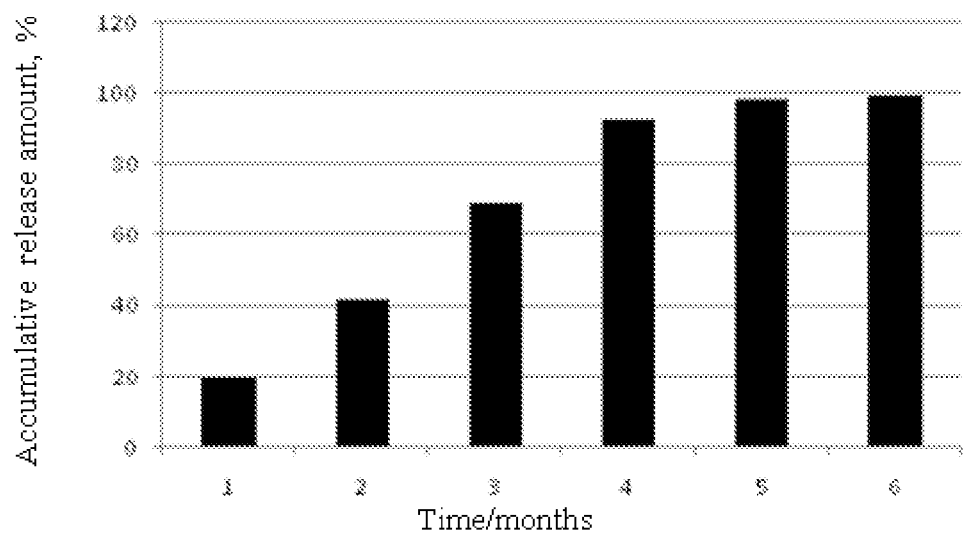
FIG. 6 shows a schematic diagram of intravitreal release amount of the ophthalmic preparation 36 in rabbit eye in Experimental Example 7.
Figure 7:
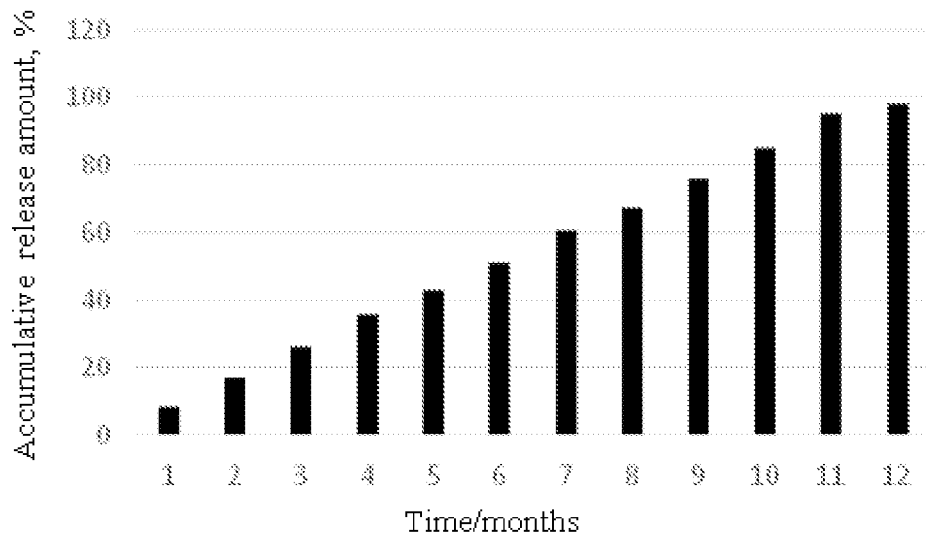
FIG. 7 shows a schematic diagram of intravitreal release amount of the ophthalmic preparation 37 in rabbit eye in Experimental Example 7.
Figure 8:
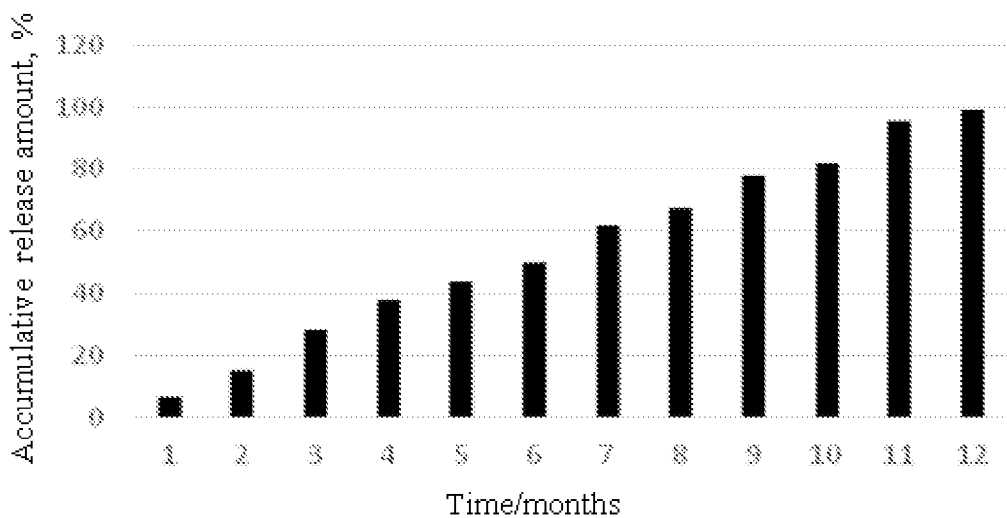
FIG. 8 shows a schematic diagram of intravitreal release amount of the ophthalmic preparation 38 in rabbit eye in Experimental Example 7.
Figure 9:
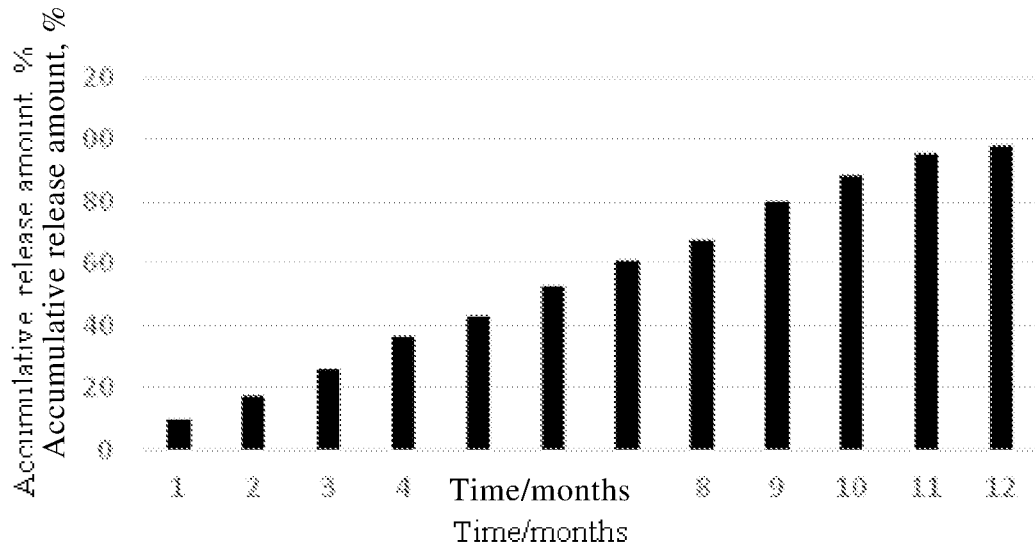
FIG. 9 shows a schematic diagram of intravitreal release amount of the ophthalmic preparation 39 in rabbit eye in Experimental Example 7.

In the following, the technical solutions in the examples of the present invention are clearly and completely described with reference to the drawings in the examples of the present invention. Obviously, the described examples are only part of examples of the present invention, but not all of the examples. The following description for at least one exemplary example is actually merely illustrative and is in no way intended to limit the invention and its application or uses. Based on the examples of the present invention, all other examples obtained by a person of ordinary skill in the art without creative efforts shall fall within the protection scope of the present invention.

The materials used in the following Preparation Examples and Comparative Examples are as follows:

PEG200: having a number average molecular weight of 190 to 210.

PEG300: having a number average molecular weight of 300.

PEG400: having a number average molecular weight of 380 to 420.

PEG600: having a number average molecular weight of 570 to 630.

Polyethylene glycol 2000: having a number average molecular weight of 1800 to 2200.

Polylactic acid-co-glycolic acid copolymer: having a weight average molecular weight of 5000 to 50,000, in which the mass ratio of polylactic acid to glycolic acid in the copolymer is 1:3.

Polylactic acid: having a weight average molecular weight of 3,000 to 60,000.

Polyglycolic acid: having a weight average molecular weight of 5000 to 50,000.

Preparation Examples 1 to 17: Preparation of Ophthalmic Preparations 1 to 17

According to the formula in Table 1, the polylactic acid-co-glycolic acid copolymer was weighed and placed into a beaker, the liquid matrix at formula amount was added thereto, and stirred at 60° C. until the polylactic acid-co-glycolic acid copolymer was completely dissolved, then the drug at formula amount was added thereto under stirring, continuously stirred until the mixture was uniform, and the mixture was filled into 1 mL glass syringes, each having a packaging volume of 200 μL. After sterilization at 121° C. for 15 minutes, the ophthalmic preparations 1 to 17 were obtained.

TABLE 1

| Ophthalmic preparation | Drug | First liquid matrix | Second liquid matrix | Solid matrix | Mass ratio* |
|---|---|---|---|---|---|
| 1 | Dexamethasone | — | PEG400 | Polylactic acid-co-glycolic acid copolymer | 1:0.1:0.1 |

TABLE 1-continued

| Ophthalmic preparation | Drug | First liquid matrix | Second liquid matrix | Solid matrix | Mass ratio* |
|---|---|---|---|---|---|
| 2 | Dexamethasone | — | PEG400 | Polylactic acid-co-glycolic acid copolymer | 1:1:0.5 |
| 3 | Dexamethasone | — | PEG400 | Polylactic acid-co-glycolic acid copolymer | 1:20:2 |
| 4 | Dexamethasone | — | Glycerol | Polylactic acid-co-glycolic acid copolymer | 1:5:2 |
| 5 | Dexamethasone | Dimethyl glutarate | — | Polylactic acid-co-glycolic acid copolymer | 1:3:0.1 |
| 6 | Dexamethasone | Diethyl succinate | — | Polylactic acid-co-glycolic acid copolymer | 1:1:0.5 |
| 7 | Dexamethasone | Diethyl succinate | — | Polylactic acid-co-glycolic acid copolymer | 1:20:2 |
| 8 | Dexamethasone | Diethyl succinate | — | Polylactic acid-co-glycolic acid copolymer | 1:5:2 |
| 9 | Dexamethasone | Diethyl succinate | — | Polylactic acid-co-glycolic acid copolymer | 1:1:1 |
| 10 | Dexamethasone | Diethyl tartarate | — | Polylactic acid-co-glycolic acid copolymer | 1:10:1 |
| 11 | Dexamethasone | Dimethyl glutarate | — | Polylactic acid-co-glycolic acid copolymer | 1:3:1 |
| 12 | Dexamethasone | Glycerol triacetate | — | Polylactic acid-co-glycolic acid copolymer | 1:20:2 |
| 13 | Dexamethasone | Diethyl succinate | PEG400 | Polylactic acid-co-glycolic acid copolymer | 1:3:7:2 |
| 14 | Dexamethasone | Diethyl succinate | PEG400 | Polylactic acid-co-glycolic acid copolymer | 1:8:2:2 |
| 15 | Dexamethasone | Dimethyl glutarate | PEG400 | Polylactic acid-co-glycolic acid copolymer | 1:9:1:1 |
| 16 | Dexamethasone | Glycerol triacetate | PEG400 | Polylactic acid-co-glycolic acid copolymer | 1:3:1:1 |
| 17 | Dexamethasone | Diethyl succinate | PEG600 | Polylactic acid-co-glycolic acid copolymer | 1:3:7:2 |

*indicates the mass ratio of the drug, the first liquid matrix or the second liquid matrix and the solid matrix, or the mass ratio of the drug, the first liquid matrix, the second liquid matrix and the solid matrix.

Preparation Example 18: Preparation of Ophthalmic Preparation 18

50 g of polylactic acid-co-glycolic acid copolymer was weighed, put in a beaker, added 50 g of PEG400 thereto, and stirred at 60° C. until the polylactic acid-co-glycolic acid copolymer was completely dissolved, and added 20 g of dexamethasone thereto under stirring, stirred continuously until the dexamethasone and the above solution were mixed uniformly to obtain the ophthalmic preparation 18.

Preparation Example 19: Preparation of Ophthalmic Preparation 19

25 g of polylactic acid-co-glycolic acid copolymer was weighed, put in a beaker, added 50 g of PEG200 thereto, and stirred at 60° C. until the polylactic acid-co-glycolic acid copolymer was completely dissolved, and added 50 g of dexamethasone thereto under stirring, stirred continuously until the dexamethasone and the above solution were mixed uniformly to obtain the ophthalmic preparation 19.

Preparation Example 20: Preparation of Ophthalmic Preparation 20

100 g of polylactic acid-co-glycolic acid copolymer was weighed, put in a beaker, added 1000 g of PEG400 thereto, and stirred at 60° C. until the polylactic acid-co-glycolic acid copolymer was completely dissolved, and added 50 g of dexamethasone thereto under stirring, stirred continuously until the dexamethasone and the above solution were mixed uniformly to obtain the ophthalmic preparation 20.

Preparation Example 21: Preparation of Ophthalmic Preparation 21

100 g of polylactic acid-co-glycolic acid copolymer was weighed, put in a beaker, added 250 g of PEG300 thereto, and stirred at 60° C. until the polylactic acid-co-glycolic acid copolymer was completely dissolved, and added 50 g of dexamethasone thereto under stirring, stirred continuously until the dexamethasone and the above solution were mixed uniformly to obtain the ophthalmic preparation 21.

Preparation Example 22: Preparation of Ophthalmic Preparation 22

5 g of polylactic acid-co-glycolic acid copolymer was weighed, put in a beaker, added 5 g of PEG400 thereto, and stirred at 60° C. until the polylactic acid-co-glycolic acid copolymer was completely dissolved, and added 50 g of dexamethasone thereto under stirring, stirred continuously until the dexamethasone and the above solution were mixed uniformly to obtain the ophthalmic preparation 22.

Preparation Example 23: Preparation of Ophthalmic Preparation 23

4950 g of polylactic acid-co-glycolic acid copolymer was weighed, put in a beaker, added 2250 g of PEG600 thereto, and stirred at 60° C. until the polylactic acid-co-glycolic acid copolymer was completely dissolved, and added 50 g of dexamethasone thereto under stirring, stirred continuously until the dexamethasone and the above solution were mixed uniformly to obtain the ophthalmic preparation 23.

Preparation Example 24: Preparation of Ophthalmic Preparation 24

30 g of polylactic acid-co-glycolic acid copolymer was weighed, added 40 g of PEG400 thereto, and added 20 g of triamcinolone acetonide thereto under stirring, stirred evenly, filled into 1 ml glass syringes, each having a packaging volume of 150 μL, and sterilized at 121° C. for 15 min to obtain the ophthalmic preparation 24.

Preparation Example 25: Preparation of Ophthalmic Preparation 25

25 g of polylactic acid was weighed, added 40 g of PEG400 and 10 g of PEG600 thereto, and added 50 g of gefitinib thereto under stirring, stirred evenly, filled into 1 ml glass syringes, each having a packaging volume of 200 μL, and sterilized at 121° C. for 15 min to obtain the ophthalmic preparation 25.

Preparation Example 26: Preparation of Ophthalmic Preparation 26

10 g of polylactic acid-co-glycolic acid copolymer was weighed, added 10 g of PEG400 thereto, and added 5 g of sunitinib thereto under stirring, stirred evenly, filled into 0.5 ml prefilled glass syringes, each having a packaging volume of 0.15 mL to obtain the ophthalmic preparation 26.

Preparation Example 27: Preparation of Ophthalmic Preparation 27

10 g of polylactic acid-co-glycolic acid copolymer was weighed, added 5 g of glycerol and 5 g of PEG600 thereto, and added 5 g of bromfenac sodium thereto under stirring, stirred evenly, filled into 1 ml glass syringes, each having a packaging volume of 200 μL, and sterilized at 121° C. for 15 min to obtain the ophthalmic preparation 27.

Preparation Example 28: Preparation of Ophthalmic Preparation 28

20 g of polylactic acid-co-glycolic acid copolymer was weighed, added 15 g of propylene glycol and 25 g of PEG300 thereto, and added 10 g of timolol thereto under stirring, stirred evenly, filled into 1 ml glass syringes, each having a packaging volume of 200 μL, and sterilized at 121° C. for 15 min to obtain the ophthalmic preparation 28.

Preparation Example 29: Preparation of Ophthalmic Preparation 29

10 g of polyglycolic acid was weighed, added 25 g of PEG400 thereto, stirred at 65° C. until the polyglycolic acid was completely dissolved, and added 5 g of irinotecan thereto under stirring, stirred continuously until the irinotecan and the above matrix were mixed uniformly, filled into 1 ml prefilled glass syringes by an automatic filling machine, each having a packaging volume of 0.2 mL, and sterilized at 121° C. for 15 min to obtain the ophthalmic preparation 29.

Preparation Example 30: Preparation of Ophthalmic Preparation 30

10 g of polylactic acid-co-glycolic acid copolymer was weighed, added 5 g of glycerol and 10 g of PEG600 thereto, added 5 g of sirolimus thereto under stirring, stirred evenly, filled into 0.5 ml prefilled glass syringes by an automatic filling machine, each having a packaging volume of 0.15 mL, and sterilized at 121° C. for 15 min to obtain the ophthalmic preparation 30.

Preparation Example 31: Preparation of Ophthalmic Preparation 31

20 g of polylactic acid-co-glycolic acid copolymer was weighed, added 30 g of glycerol triacetate thereto, added 1 g of latanoprost thereto under stirring, stirred evenly, filled into 1 ml glass syringes, and sterilized to obtain the ophthalmic preparation 31.

Preparation Example 32: Preparation of Ophthalmic Preparation 32

50 g of polylactic acid-co-glycolic acid copolymer was weighed, added 100 g of glycerol triacetate thereto, added 40 g of dasatinib thereto under stirring, stirred evenly, filled into 1 ml glass syringes, and sterilized to obtain the ophthalmic preparation 32.

Preparation Example 33: Preparation of Ophthalmic Preparation 33

2 g of polylactic acid was weighed, added 1 g of PEG400 thereto, added 1 g of triamcinolone acetonide thereto under stirring, stirred evenly, filled into 1 ml glass syringes, and sterilized to obtain the ophthalmic preparation 33.

Preparation Example 34: Preparation of Ophthalmic Preparation 34

4 g of polylactic acid-co-glycolic acid copolymer was weighed, added 4 g of PEG400, 0.5 g of glycerol and 0.5 g of propylene glycol thereto, added 4 g of paclitaxel thereto under stirring, stirred evenly, filled into 1 ml glass syringes, and sterilized to obtain the ophthalmic preparation 34.

Preparation Example 35: Preparation of Ophthalmic Preparation 35

6 g of polylactic acid-co-glycolic acid copolymer was weighed, added 9 g of PEG400 thereto, added 6 g of dexamethasone thereto under stirring, stirred evenly, filled into 1 ml glass syringes, and sterilized to obtain the ophthalmic preparation 35.

Preparation Examples 36 to 39: Preparation of Ophthalmic Preparations 36 to 39

30 g of polylactic acid-co-glycolic acid copolymer was weighed, added 10 g of PEG400 thereto, then added 30 g of diethyl succinate, 30 g of diethyl tartarate, 30 g of dimethyl glutarate or 30 g of glycerol triacetate thereto respectively, added 30 g of triamcinolone acetonide thereto under stirring, stirred evenly, filled into 1 ml glass syringes, each having a packaging volume of 150 μL, and sterilized at 121° C. for 15 min to obtain the ophthalmic preparations 36 to 39 respectively.

Preparation Example 40: Preparation of Ophthalmic Preparation 40

30 g of polylactic acid-co-glycolic acid copolymer was weighed, added 40 g of PEG400 thereto, added 30 g of triamcinolone acetonide thereto under stirring, stirred evenly, filled into prefilled glass syringes to obtain the ophthalmic preparation 40.

Preparation Examples 41 to 44: Preparation of Ophthalmic Preparations 41 to 44

40 g of polylactic acid-co-glycolic acid copolymer, 40 g of polylactic acid, 40 g of polyglycolic acid and 40 g of polyethylene glycol 2000 were weighed respectively, added 40 g of PEG400 thereto respectively, then added 20 g of dexamethasone thereto respectively under stirring, stirred evenly, filled into prefilled glass syringes to obtain the ophthalmic preparations 41 to 44.

Experimental Example 1: Observation of the Status of Ophthalmic Preparations in Rabbit Eye Vitreum or Rabbit Eye Anterior Chamber (1) 50 μL of the ophthalmic preparations 1 to 17 and 33 to 35 were injected into the rabbit eye vitreum respectively, and the status of the ophthalmic preparations in the rabbit eye vitreum was observed.

It was found that the ophthalmic preparations 1 to 17 aggregated in the rabbit eye vitreum without dispersing, while the ophthalmic preparations 33 to 35 automatically aggregated into a spherical shape in the rabbit eye vitreum.

(2) 20 μL of the ophthalmic preparations 26 and 30 were injected into the rabbit eye anterior chamber respectively, and the status of the preparations in the rabbit eye anterior chamber was observed.

It was found that the ophthalmic preparations 26 and 30 automatically aggregated into a spherical shape in the rabbit eye anterior chamber.

Experimental Example 2: Observation of the Status of Ophthalmic Preparations in Sodium Chloride Solution or Phosphate Buffer Solution (1) 50 μL of the ophthalmic preparations 18 to 23 and 36 to 39 were injected respectively into beakers with 0.9% sodium chloride solution at pH=7.4 and osmotic pressure=292 mOsmol/kg, and the status of each in sodium chloride solution was observed.

It was found that the ophthalmic preparations 18 to 23 and 36 to 39 automatically aggregated into a spherical shape in sodium chloride solution and deposited on the bottom of the beakers.

(2) 100 μL of the ophthalmic preparations 24 to 25, 27 to 28, and 31 to 32 were injected respectively into breakers with phosphate buffer solution at pH=7.4 and osmotic pressure=292 mOsmol/kg (the pH of 50 mmol/L potassium dihydrogen phosphate was adjusted to 7.4 with hydroxide sodium), and the status of each in phosphate buffer solution was observed.

It was found that the ophthalmic preparations 24 to 25, 27 to 28, and 31 to 32 automatically aggregated into a spherical shape in phosphate buffer solution and deposited on the bottom of the beakers.

Experimental Example 3: Investigation of In Vitro Release Rate of Ophthalmic Preparations 50 μL of the ophthalmic preparation 24 and the ophthalmic preparations 36 to 39 were taken and injected into breakers with 200 mL of release medium (sodium chloride solution, containing 0.01% benzalkonium chloride, pH=7.4, osmotic pressure=292 mOsmol/kg), respectively. The beakers were placed in a gas bath oscillator, the temperature was controlled at 37±0.5° C., 10 mL of release medium was taken at different times and an equal amount of release medium was supplemented. The release medium was filtered through a 0.22 μm microporous filter membrane, and the triamcinolone acetonide content in the release medium was determined by a high performance liquid chromatography (HPLC) method.

Chromatographic conditions: Ultimate, XB-C18 column (4.6×250 mm, 5 μm); mobile phase:methanol-water (52.5: 47.5, v/v); detection wavelength: 240 nm; column temperature: 30° C.; flow rate: 1.0 mL·min$^{-1}$; injection volume: 20 μL.

The cumulative release amount Rn % of the drug was calculated according to the following formula. The results are shown in FIGS. 1 to 5.

$$Rn\% = \left(C_n V_0 + \sum_{n=1}^{n} C_{n-1} V\right) / M_t \times 100\%$$

wherein, $V_0$ is the release medium volume, $C_n$ is the drug concentration in the $n^{th}$ sampling, V is the sampling volume, and $M_t$ is the total drug concentration.

Comparing the release results in FIGS. 1 to 5, it could be found that when using PEG400 together with diethyl succinate, diethyl tartrate, dimethyl glutarate, or glycerol triacetate as the liquid matrix, the sustained-release rate of the ophthalmic preparation was reduced, the sustained-release effect of a single administration could last about 1 year.

When the ophthalmic preparations 31 to 32 were used for the in vitro release test, the sustained-release effect of a single administration could last 200 days.

Experimental Example 4: Observation of Appearance Change of Ophthalmic Preparations after being Injected into Rabbit Eye Anterior Chamber 25 μL of the ophthalmic preparations 31 to 32, 36 to 39 and 40 were injected into the rabbit eye anterior chamber respectively, and the changes of the preparations in the rabbit eyes were observed every other day with a hand-held slit lamp.

The results showed that:

After injection, the ophthalmic preparations 31 to 32 aggregated into spherical milky white solid particles and gradually subsided in the lower part of the anterior chamber. With the extension of time, the volume of solid particles gradually decreased. On the 80th to 85th days, the solid particles completely disappeared.

After injection, the ophthalmic preparations 36 to 39 aggregated into spherical milky white solid particles and gradually subsided in the lower part of the anterior chamber. With the extension of time, the volume of solid particles gradually decreased. On the 100th day, the solid particles completely disappeared.

After injection, the ophthalmic preparation 40 aggregated into spherical milky white solid particles and gradually subsided in the lower part of the anterior chamber. With the extension of time, the volume of solid particles gradually decreased, and the solid particles completely disappeared on the $92^{nd}$ to $97^{th}$ days.

These observation results indicated that the ophthalmic preparations prepared by the above method could be slowly degraded in the living body so as to continuously release the active ingredient.

Experimental Example 5: Observation of the Appearance Change of Ophthalmic Preparations after being Injected into Rabbit Eye Vitreum 25 μL of the ophthalmic preparations 31 to 32, 36 to 39 and 40 were injected into the rabbit eye vitreum respectively, and the changes of the preparations in the rabbit eyes were observed every other day with a handheld slit lamp.

The results showed that:

After injection, the ophthalmic preparations 31 to 32 aggregated into spherical milky white solid particles and remained at the injection site. With the extension of time, the volume of solid particles gradually decreased. On the 180th day, the solid particles completely disappeared.

After injection, the ophthalmic preparations 36 to 39 aggregated into spherical milky white solid particles and remained at the injection site. With the extension of time, the volume of solid particles gradually decreased. On the 300th day, the solid particles completely disappeared.

After injection, the ophthalmic preparation 40 aggregated into spherical milky white solid particles and remained at the injection site. With the extension of time, the volume of solid particles gradually decreased, and the solid particles completely disappeared during the period of the $73^{rd}$ to $75^{th}$ days.

These observation results indicated that the ophthalmic preparations of the present invention could be slowly degraded in the living body so as to continuously release the active ingredient.

Experimental Example 6: Observation of the Status Change of Ophthalmic Preparations after being Injected into Rabbit Eye Tenon Capsule 100 μL of the ophthalmic preparations 31 to 32, 36 to 39 and 40 were injected into the Tenon capsules of 60 rabbits' right eyes respectively. 5 animals were sacrificed and dissected each month, and the state of the preparations in the Tenon capsules was observed.

The results showed that:

After injection of the ophthalmic preparations 31 to 32, the volume of the preparations in the Tenon capsules of rabbit eyes gradually decreased over time; among the 5 rabbits dissected in the 8th month, the preparations in the Tenon capsules of 2 rabbits had completely disappeared; and among the 5 rabbits dissected in the 9th month, the preparations in the Tenon capsules of 3 rabbits had completely disappeared, and a very small amount of the preparations remained in the Tenon capsules of the other 2 rabbits.

After injection of the ophthalmic preparations 36 to 39, the volume of the preparations in the Tenon capsules of rabbit eyes gradually decreased over time; among the 5 rabbits dissected in the $8^{th}$ month, the preparation in the Tenon capsule of 0 rabbit had completely disappeared; and among the 5 rabbits dissected in the $9^{th}$ month, the preparations in Tenon capsules of 2 rabbits had completely disappeared, and a very small amount of the preparations remained in the Tenon capsules of the other 3 rabbits.

After injection of the ophthalmic preparation 40, the volume of the preparations in the Tenon capsules of rabbit eyes gradually decreased over time; among the 5 rabbits dissected in the $8^{th}$ month, the preparation in the Tenon capsule of 1 rabbit had completely disappeared; among the 5 rabbits dissected in the $9^{th}$ month, the preparations in the Tenon capsules of 4 rabbits had completely disappeared, and a very small amount of the preparation remained in the Tenon capsule of the other 1 rabbit.

Experimental Example 7: Observation of the Release Behavior of Ophthalmic Preparation in Rabbit Eye Vitreum after Single Injection (1) 48 New Zealand rabbits were taken, randomly grouped, 4 rabbits per group. The right eyes of the rabbits in each group were injected with 50 μL of the ophthalmic preparations 36 to 39 respectively, the animals of one group were executed in each of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ months after the injection, and the unreleased preparations were removed from the vitreum. The triamcinolone acetonide contents in the preparations were determined by HPLC method, and the cumulative release amounts were calculated. The results were shown in FIGS. 6 to 9.

Figure 10:
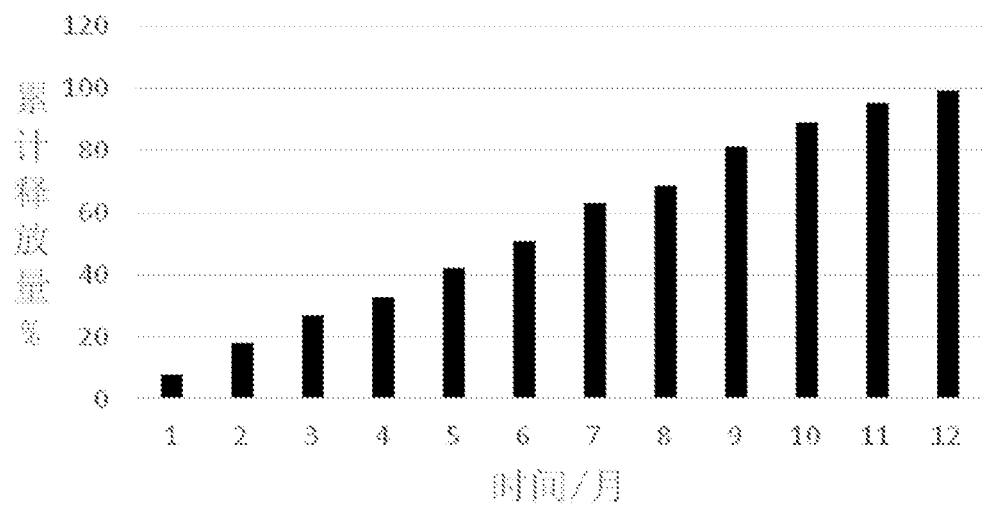
FIG. 10 shows a schematic diagram of intravitreal release amount of the ophthalmic preparation 24 in rabbit eye in Experimental Example 7.

(2) 36 New Zealand rabbits were taken, randomly grouped, 6 rabbits per group. The right eyes of the rabbits in each group were injected with 50 μL of the ophthalmic preparation 24, the animals of one group were executed in each of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ months after the injection, and the unreleased preparations were removed from the vitreum. The triamcinolone acetonide contents in the preparations were determined by HPLC method, and the cumulative release amounts were calculated. The results were shown in FIG. 10.

According to FIGS. 6 to 10, it could be seen that the sustained-release time of the ophthalmic preparations of the present invention in the rabbit eye vitreum was as long as 12 months, while the sustained-release time of the ophthalmic preparation 24 in the rabbit eye vitreum was only 6 months.

Therefore, the ophthalmic preparations of the present invention could significantly prolong the sustained-release time in the vitreum and maintain the drug efficacy for a long time.

Finally, it should be noted that the above examples are only used to illustrate the technical solutions of the present invention and are not limited them. Although the present invention has been described in detail with reference to the preferred examples, those skilled in the art should understand that the specific embodiments of the present invention could still be modified or some technical features thereof could be replaced with equivalent technical features without departing from the spirit of the technical solution of the present invention, and all of these modifications should all fall into the scope of the technical solution sought to be protected by the present invention.

What is claimed is:

1. An ophthalmic pharmaceutical composition, consisting of the following components:
   0.3 to 1.5 parts by weight of a solid matrix;
   0.8 to 2 parts by weight of a liquid matrix; and
   1 part by weight of an active pharmaceutical ingredient;
   wherein the solid matrix is polylactic acid-co-glycolic acid copolymer having a weight average molecular weight of 5000 to 50,000, in which the mass ratio of lactic acid to glycolic acid in the copolymer is 1:3,
   wherein the liquid matrix is polyethylene glycol having a number average molecular weight of 200 to 600, and
   wherein the active pharmaceutical ingredient is triamcinolone acetonide.

2. The ophthalmic pharmaceutical composition according to claim 1, wherein the ophthalmic pharmaceutical composition is an ophthalmic pharmaceutical preparation.

3. The ophthalmic pharmaceutical composition according to claim 2, wherein the ophthalmic pharmaceutical composition is an ophthalmic pharmaceutical injection preparation.

4. An ophthalmic kit comprising an ophthalmic pharmaceutical composition consisting of: 0.3 to 1.5 parts by weight of a solid matrix, 0.8 to 2 parts by weight of a liquid matrix, and 1 part by weight of an active pharmaceutical ingredient;
wherein the solid matrix is polylactic acid-co-glycolic acid copolymer having a weight average molecular weight of 5000 to 50,000, in which the mass ratio of lactic acid to glycolic acid in the copolymer is 1:3,
wherein the liquid matrix is polyethylene glycol having a number average molecular weight of 200 to 600, and
wherein the active pharmaceutical ingredient is triamcinolone acetonide.

5. The ophthalmic kit according to claim 4, having one or more of the following items i to ii:
i. the ophthalmic kit further comprises a syringe;
ii. the ophthalmic kit is an ophthalmic injection kit.

6. An ophthalmic sustained-release medicament, comprising the ophthalmic kit according to claim 4.

7. A method for preparing the ophthalmic pharmaceutical composition according to claim 1, comprising the following steps:
(1) mixing the solid matrix with the liquid matrix to obtain a mixed substance;
(2) mixing the mixed substance obtained in step (1) with the active pharmaceutical ingredient.

8. The method according to claim 7, wherein the mixing is performed at a temperature of 20° C. to 100° C. in step (1).

9. A method for treating uveitis, retinal vein occlusion, diabetic retinopathy, cataract postoperative inflammation, proliferative vitreoretinopathy, choroidal neovascularization, macular hole, cystoid macular edema, optic neuritis, or age-related macular degeneration, comprising a step of injecting the ophthalmic pharmaceutical composition according to claim 1 into an eye in need thereof.

10. The method according to claim 9, wherein the injecting is performed into a posterior segment of the eye.

* * * * *